(12) United States Patent
Govari

(10) Patent No.: US 12,728,232 B2
(45) **Date of Patent: *Sep. 8, 2026**

(54) DEFLECTABLE MEDICAL PROBE

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 727 days.

This patent is subject to a terminal disclaimer.

(21) Appl. No.: 17/991,976

(22) Filed: Nov. 22, 2022

(65) Prior Publication Data

US 2023/0078216 A1 Mar. 16, 2023

Related U.S. Application Data

(63) Continuation of application No. 15/860,235, filed on Jan. 2, 2018, now Pat. No. 11,517,715.

(51) Int. Cl.
*A61B 18/14* (2006.01)
*A61B 1/005* (2006.01)
(Continued)

(52) U.S. Cl.
CPC ....... *A61M 25/0147* (2013.01); *A61B 1/0052* (2013.01); *A61B 1/0055* (2013.01);
(Continued)

(58) Field of Classification Search
CPC A61B 2018/00357; A61B 2018/00577; A61B 2018/0016; A61B 2018/00172; A61B 2018/00952; A61B 2018/0091; A61B 2018/00916; A61B 18/1492; A61B 18/12; A61B 18/14; A61B 18/1402; A61B 2017/00323; A61B 2017/00327;
(Continued)

(56) References Cited

U.S. PATENT DOCUMENTS

| | | | |
|---|---|---|---|
| 4,734,093 A | 3/1988 | Bonello et al. | |
| 5,195,968 A * | 3/1993 | Lundquist ......... | A61M 25/0147 604/95.04 |

(Continued)

FOREIGN PATENT DOCUMENTS

| | | |
|---|---|---|
| CN | 104427950 A | 3/2015 |
| CN | 106102551 A | 11/2016 |

(Continued)

OTHER PUBLICATIONS

Search Reported dated Dec. 16, 2022, from corresponding Japanese Patent Application No. 2020-556352.

(Continued)

*Primary Examiner* — Thomas A Giuliani

(57) ABSTRACT

A medical probe includes a shaft for navigation in a patient body, and first and second deflection mechanisms. The shaft ends with a flexible section and a spring, followed by a rigid distal tip having one or more medical devices coupled thereto. The first deflection mechanism is configured to deflect the flexible section relative to the shaft. The second deflection mechanism is configured to deflect the distal tip relative to the first flexible section by using the spring.

10 Claims, 2 Drawing Sheets

(51) Int. Cl.

| | |
|---|---|
| ***A61B 1/01*** | (2006.01) |
| ***A61B 5/00*** | (2006.01) |
| ***A61B 5/287*** | (2021.01) |
| ***A61M 25/00*** | (2006.01) |
| ***A61M 25/01*** | (2006.01) |
| *A61B 17/00* | (2006.01) |
| *A61B 18/00* | (2006.01) |

(52) U.S. Cl.

CPC .............. *A61B 1/0057* (2013.01); *A61B 1/01* (2013.01); *A61B 5/287* (2021.01); *A61B 5/6852* (2013.01); *A61B 18/1492* (2013.01); *A61M 25/001* (2013.01); *A61M 25/008* (2013.01); *A61M 25/0082* (2013.01); *A61M 25/0136* (2013.01); *A61M 25/0141* (2013.01); *A61B 2017/00323* (2013.01); *A61B 2017/00327* (2013.01); *A61B 2018/00357* (2013.01); *A61B 2018/00577* (2013.01); *A61M 25/0138* (2013.01); *A61M 2025/015* (2013.01)

(58) Field of Classification Search

CPC ..... A61B 5/287; A61B 5/6852; A61B 1/0055; A61B 1/0057; A61M 25/0147; A61M 25/008; A61M 25/0082; A61M 25/0141; A61M 25/0138

USPC .......... 606/41, 45–50; 607/98, 99, 101, 113, 607/115, 116

See application file for complete search history.

(56) References Cited

U.S. PATENT DOCUMENTS

| | | | | |
|---|---|---|---|---|
| 5,242,441 | A | 9/1993 | Avitall | |
| 5,391,199 | A | 2/1995 | Ben-Haim | |
| 5,431,168 | A | 7/1995 | Webster, Jr. | |
| 5,449,369 | A | 9/1995 | Imran | |
| 5,882,333 | A * | 3/1999 | Schaer | A61M 25/0147 604/95.01 |
| 6,033,378 | A | 3/2000 | Lundquist et al. | |
| 6,183,435 | B1 | 2/2001 | Bumbalough et al. | |
| 6,198,974 | B1 | 3/2001 | Webster, Jr. | |
| 6,239,724 | B1 | 5/2001 | Poron et al. | |
| 6,332,089 | B1 | 12/2001 | Acker et al. | |
| 6,484,118 | B1 | 11/2002 | Govari | |
| 6,618,612 | B1 | 9/2003 | Acker et al. | |
| 6,690,963 | B2 | 2/2004 | Ben-Haim et al. | |
| 7,682,319 | B2 | 3/2010 | Martin et al. | |
| 8,236,010 | B2 | 8/2012 | Ortiz et al. | |
| 10,046,141 | B2 | 8/2018 | Schultz | |
| 10,814,098 | B2 | 10/2020 | Schaeffer | |
| 11,517,715 | B2 * | 12/2022 | Govari | A61M 25/0141 |
| 2002/0065455 | A1 | 5/2002 | Ben-Haim et al. | |
| 2002/0077590 | A1 | 6/2002 | Ponzi et al. | |
| 2002/0095102 | A1 | 7/2002 | Winters | |
| 2003/0120150 | A1 | 6/2003 | Govari | |
| 2004/0068178 | A1 | 4/2004 | Govari | |
| 2006/0074383 | A1 | 4/2006 | Boulais | |
| 2007/0156116 | A1 * | 7/2007 | Gonzalez | A61B 1/008 604/528 |
| 2007/0225681 | A1 | 9/2007 | House | |
| 2009/0171275 | A1 | 7/2009 | Ostrovsky et al. | |
| 2009/0240110 | A1 * | 9/2009 | Miyawaki | A61B 1/0055 600/149 |
| 2010/0121269 | A1 | 5/2010 | Goldenberg et al. | |
| 2013/0205937 | A1 | 8/2013 | Arai | |
| 2013/0317375 | A1 | 11/2013 | Garcia et al. | |
| 2014/0165772 | A1 | 6/2014 | Okazaki | |
| 2015/0066014 | A1 | 3/2015 | Sliwa et al. | |
| 2015/0157381 | A1 | 6/2015 | Ashton et al. | |
| 2015/0246205 | A1 | 9/2015 | Schaeffer | |
| 2015/0335862 | A1 | 11/2015 | Selkee | |
| 2016/0339207 | A1 | 11/2016 | Beeckler et al. | |
| 2017/0007803 | A1 * | 1/2017 | Ostrovsky | A61M 25/0138 |
| 2021/0127951 | A1 | 5/2021 | Akui | |

FOREIGN PATENT DOCUMENTS

| | | |
|---|---|---|
| CN | 107252517 A | 10/2017 |
| CN | 107454854 A | 12/2017 |
| JP | H05507212 A | 10/1993 |
| JP | H10500334 A | 1/1998 |
| JP | 2013244413 A | 12/2013 |
| WO | WO 95/31243 A1 | 11/1995 |
| WO | WO 96/05768 A1 | 2/1996 |

OTHER PUBLICATIONS

Notice of Reasons for Refusal dated Jan. 17, 2023, from corresponding Japanese Patent Application No. 2020-556352.

Written Opinion dated Apr. 14, 2023, from corresponding Japanese Application No. 2020-556352.

Decision to Grant Patent dated Jul. 4, 2023, from corresponding Japanese Application No. 2020-556352.

International Search Report issued in International Patent Application No. PCT/1B2018/060307 dated Apr. 15, 2019.

First Search English translation dated Jan. 19, 2024, from corresponding Chinese Application No. 201880085149.0.

First Office Action with English translation dated Jan. 19, 2024, from corresponding Chinese Application No. 201880085149.0.

Second Search English translation dated Apr. 3, 2024, from corresponding Chinese Application No. 201880085149.0.

Second Office Action with English translation dated Apr. 3, 2024, from corresponding Chinese Application No. 201880085149.0.

* cited by examiner 20
24
34
42
48
46
44
22
30
32
23
22
40
26
22
29
28
38
36
36

DEFLECTABLE MEDICAL PROBE

CROSS REFERENCE TO RELATED APPLICATION

The present application is a continuation application of U.S. patent application Ser. No. 15/860,235 filed Jan. 2, 2018, now U.S. Pat. No. 11,517,715 issued Dec. 6, 2022. The entire contents of which are hereby incorporated by reference.

FIELD OF THE INVENTION

The present invention relates generally to medical probes, and particularly to methods and systems for deflecting medical probe distal ends.

BACKGROUND OF THE INVENTION

Medical probes, such as deflectable catheters, are used in some medical applications. Various types of deflectable catheters are known in the art.

For example, U.S. Pat. No. 5,431,168 describes a steerable catheter comprising an elongated catheter body and a tip portion. First and second lumens extend through the catheter body and tip portion. The first lumen is open at the distal end of the catheter. The second lumen is off-axis.

U.S. Pat. No. 5,242,441 describes a cardiac arrhythmia ablation catheter that has a highly flexible tubular distal segment particularly adapted for navigating and exploring a ventricular cardiac chamber.

U.S. Patent Application Publication 2002/0077590 describes a deflectable catheter comprising a catheter body, a tip section, and a control handle for affecting deflection of the tip section. The tip section comprises a flexible tubing having proximal and distal ends and at least two lumens extending therethrough.

SUMMARY OF THE INVENTION

An embodiment of the present invention that is described herein provides a medical probe including a shaft for navigation in a patient body, and first and second deflection mechanisms. The shaft ends with a flexible section and a spring, followed by a rigid distal tip having one or more medical devices coupled thereto. The first deflection mechanism is configured to deflect the flexible section relative to the shaft. The second deflection mechanism is configured to deflect the distal tip relative to the first flexible section by using the spring.

In some embodiments, the first deflection mechanism includes one or more wires coupled to the flexible section. In other embodiments, the medical probe includes a device external to the patient body, the wires extend between the flexible section and the device, and the device is configured to deflect the flexible section relative to the shaft by applying a force to at least one of the wires. In yet other embodiments, the force includes a pulling force.

In an embodiment, the second deflection mechanism includes one or more other wires coupled to the distal tip. In another embodiment, the medical probe includes a device external to the patient body, the other wires extend between the distal tip and the device, and the device is configured to deflect the distal tip relative to the flexible section by applying a force to at least one of the other wires.

In some embodiments, the force includes a pulling force. In other embodiments, the medical probe includes a handle, which is coupled to at least one of the first and second deflection mechanism, and which is configured to deflect at least one of the distal tip and the flexible section, using, respectively, one or more of the first and second deflection mechanisms.

There is additionally provided, in accordance with an embodiment of the present invention, a method for producing a medical probe, the method includes assembling a shaft ending with a flexible section and a spring, followed by a rigid distal tip having one or more medical devices coupled thereto. First and second deflection mechanisms are connected to the medical probe, the first deflection mechanism deflects the flexible section relative to the shaft, and the second deflection mechanism deflects the distal tip relative to the first flexible section.

The present invention will be more fully understood from the following detailed description of the embodiments thereof, taken together with the drawings in which:

DETAILED DESCRIPTION OF EMBODIMENTS

Overview

Figure 1:
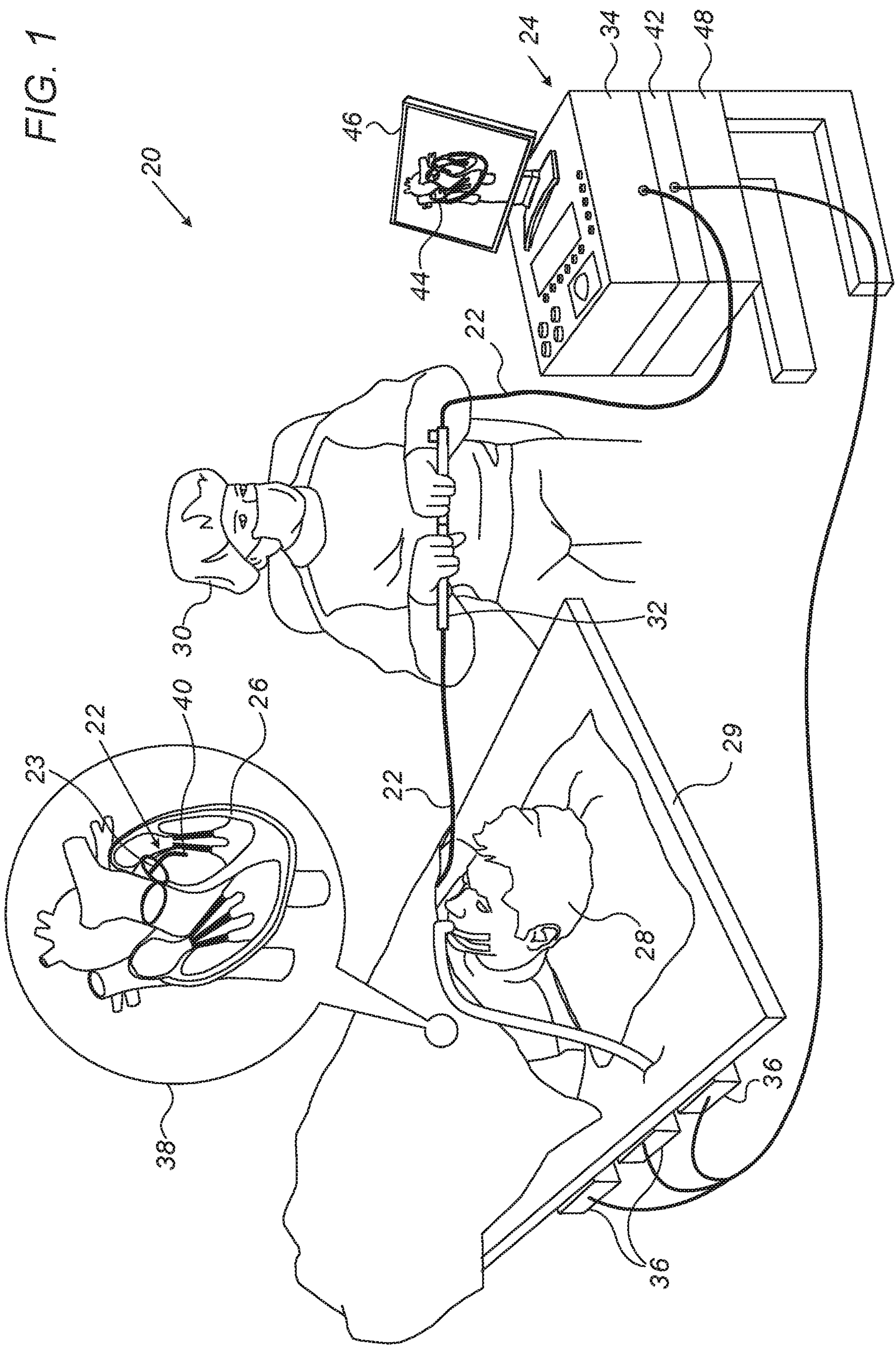
FIG. 1 is a schematic, pictorial illustration of a catheterization system, in accordance with an embodiment of the present invention.

Some medical procedures, such as cardiac electrophysiology (EP) and sinuplasty, may involve navigating a medical probe to a target location in an organ of a patient. In some cases, a physician that carries out the procedure may face challenges in navigating the probe into the organ in question and in setting the probe at the target location. For example, forcing the catheter into the patient body may cause damage to the organ tissue. Furthermore, in some procedures it is important to approach the tissue with the probe from a desired angle and to make a proper physical contact between the probe and tissue at the target location.

Embodiments of the present invention address these challenges, by providing a medical probe having a flexible distal end assembly that comprises multiple deflectable sections coupled along a longitudinal axis of the probe, each section is configured to deflect independently of the other section or sections using a different deflection mechanism.

In some embodiments, the probe comprises a rigid distal tip having one or more medical devices, such as sensing electrodes, coupled to an external surface of the distal tip. In an embodiment, the distal tip may have a hollow profile so as to enable passage of leads coupled to the electrodes. The leads are configured to conduct electrical signals between the electrodes and a computer coupled to the proximal end of the probes.

In some embodiments, the probe comprises a shaft for navigating the probe in a patient body. The shaft ends with a hollow flexible section and a spring, followed by the distal tip. The flexible section has some inherent level of flexibility that allows some deflection in response to bending forces applied to the flexible section, for example, using a manipulator device located at the proximal end of the probe.

In some embodiments, the spring connects between the distal tip and the flexible section, along the longitudinal axis of the medical probe. In response to bending forces applied to the flexible section, the spring is configured to deflect the distal tip relative to the flexible section of the probe.

In some embodiments, the medical probe comprises one or more pulling wires coupled, at respective coupling locations, to the inner surfaces of the hollow distal tip and flexible section. The pulling wires are adapted, when pulled by the physician, to apply bending forces that induce deflection of the flexible section relative to shaft, and deflection of the distal tip relative to the flexible section. The physician may control the degree of deflection by controlling the pulling force applied to each of the pulling wires.

Note that typically the distal tip is coupled to one set of one or more pulling wires, and the flexible section is coupled to another set of one or more pulling wires, so that the distal tip and flexible section can be deflected independently of one another.

In some embodiments, the pulling wires may be coupled to a manipulator device, also referred to herein as a handle, which is coupled to the proximal end of the medical probe, so as to control the levels of deflection caused to the distal tip and the flexible section using a single manipulator device.

In some embodiments, the probe may comprise any suitable number of pulling wires coupled to the inner surface at any suitable configuration, so as to control the angles and levels of deflection of the distal tip and the flexible section.

The disclosed techniques increase the maneuverability and functionality of medical catheters by enabling improved flexibility of the distal end assembly, and independent manipulation of multiple sections along the longitudinal axis of the probe.

System Description

FIG. 1 is a schematic, pictorial illustration of a catheterization system 20, in accordance with an embodiment of the present invention. System 20 comprises a probe, in the present example a cardiac catheter 22, and a control console 24.

In the embodiment described herein, catheter 22 may be used for any suitable therapeutic and/or diagnostic purposes, such as for sensing electro-potential signals or for ablating tissue in a heart 26 of a patient 28.

In some embodiments, console 24 comprises a processor 34, typically a general-purpose computer, with suitable front end and interface circuits for receiving signals from catheter 22 and for controlling the other components of system 20 described herein.

In some embodiments, console 24 further comprises a memory 48, and a display 46, which is configured to display data, such as an image 44 of at least part of heart 26 of patient 28. In some embodiments, image 44 may be acquired using any suitable anatomical imaging system, such as computerized tomography (CT) or fluoroscopic imaging.

A physician 30, inserts catheter 22 through the vascular system of patient 28 lying on a table 29.

Reference is now made to an inset 38. In some embodiments, catheter 22 comprises a shaft 23 for navigation the catheter in a patient body. In some embodiments, shaft 23, or any other suitable component of catheter 22, is coupled to a distal-end assembly 40, depicted in detail in FIG. 2 below. Physician 30 moves assembly 40 in the vicinity of the target region in heart 26 by manipulating shaft 23 of catheter 22 using a manipulator 32 coupled near the proximal end of catheter 22. The proximal end of catheter 22 is connected to interface circuitry of processor 34.

In some embodiments, the position of distal-end assembly 40 in the heart cavity is typically measured using position sensing techniques. This method of position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In some embodiments, console 24 comprises a driver circuit 42, which drives magnetic field generators 36 placed at known positions external to patient 28, e.g., below the patient's torso.

In some embodiments, processor 34 is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Deflecting the Distal End Assembly of the Medical Probe

Figure 2:
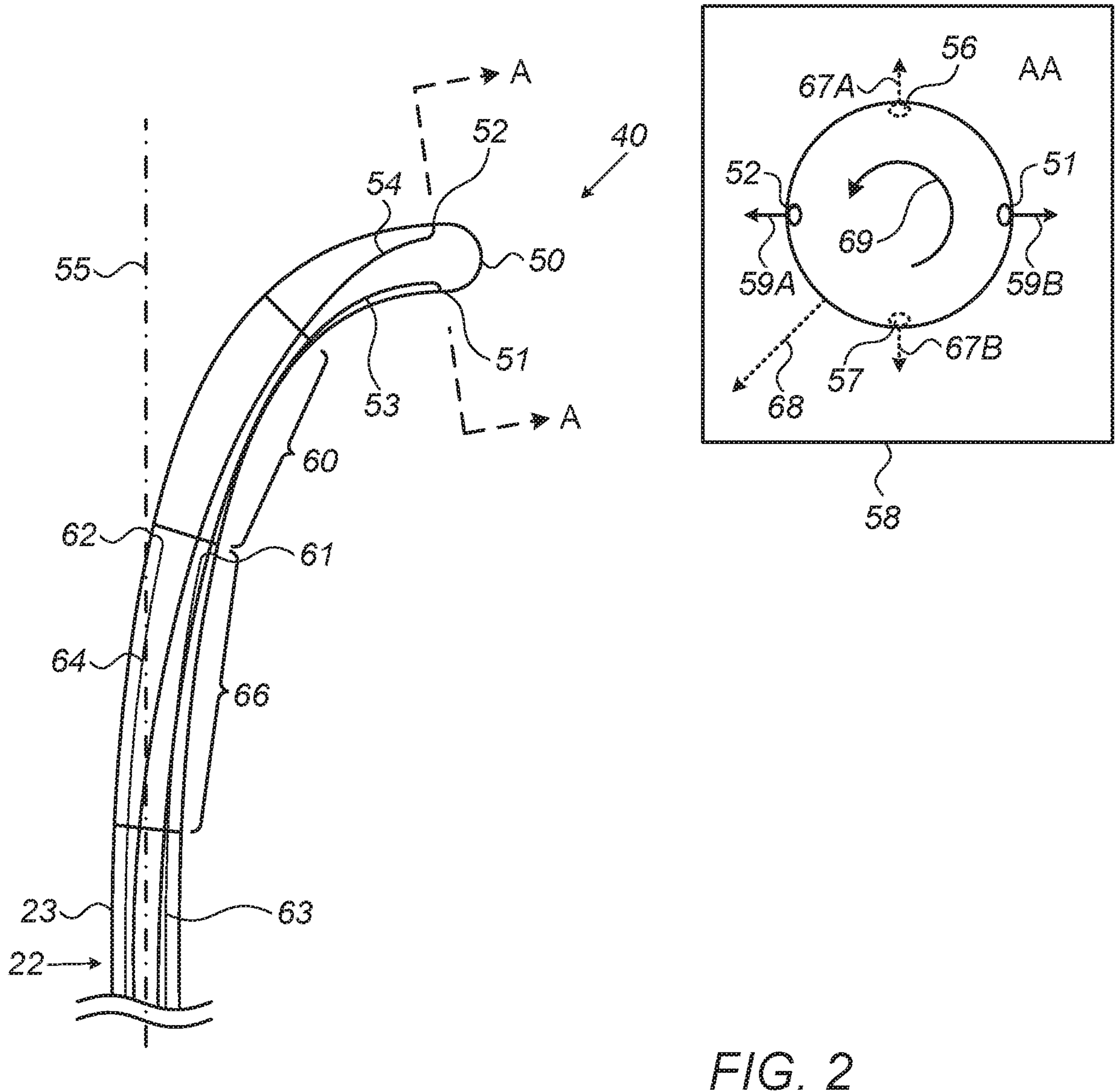
FIG. 2 is a schematic, pictorial illustration of a deflectable distal end assembly of a catheter, in accordance with an embodiment of the present invention.

FIG. 2 is a schematic, pictorial illustration of distal end assembly 40, in accordance with an embodiment of the present invention. In some embodiments, distal end assembly 40 comprises a rigid distal tip 50 made from any suitable rigid material such as metal or plastic.

In some embodiments, distal tip 50 comprises one or more electrodes (not shown), coupled to the outer surface of distal tip 50 and configured to exchange, via catheter 22, electrical signals between console 24 and the tissue of heart 26. The electrodes may be used for sensing signals from heart 26, and/or for applying ablation signals for ablating the tissue of heart 26.

In some embodiments, distal tip 50 may be hollow, so as to enable passage of electrical leads configured to conduct the electrical signals between console 24 and the electrodes. In other embodiments, distal tip 50 may comprise a flexible substrate, e.g., a flexible printed circuit board (PCB), wrapped around a solid profile of tip 50. In these embodiments, the PCB may comprise the leads formed thereon, and the electrodes formed and/or mounted thereon.

In some embodiments, distal tip 50 may have a tubular shape as shown in FIG. 2, or any other suitable shape, such as a balloon shape, a lasso, or a basket catheter.

In some embodiments, distal end assembly 40 comprises a hollow flexible section 66, which is coupled to shaft 23 of catheter 22 along a longitudinal axis 55 of assembly 40, and is configured to deflect relative to shaft 23 in response to a bending force, as will be described below. Note that in a non-deflected position (e.g., when assembly 40 is inserted into the body of patient 28,) flexible section 66 is typically aligned with distal tip 50 and with shaft 23, along longitudinal axis 55.

In some embodiments, distal end assembly 40 comprises a spring 60, which is coupled to distal tip 50 at one end of the spring and to flexible section 66 at the opposite end of the spring, along longitudinal axis 55.

In some embodiments, spring 60 is configured to enable deflection of distal tip 50 relative to flexible section 66. In some embodiments, flexible section 66 and spring 60 are hollow, so as to allow passage of the electrical leads between catheter 22 and distal tip 50.

In some embodiments, distal end assembly 40 comprises a pair of pulling wires 53 and 54, and a pair of pulling wires 63 and 64. Each pair serves as a, typically independent, deflection mechanism. In these embodiments, wires 53 and 54 are adapted to deflect distal tip 50 relative to flexible section 66, thereby serving as one deflection mechanism, whereas wires 63 and 64 are adapted to deflect flexible section 66 relative to shaft 23, thereby serving a different deflection mechanism. In the example of FIG. 2, wires 53 and 63 are coupled to one section (referred to herein as the "right section") of the inner surface of assembly 40, and wires 54 and 64 are coupled to an opposite section (referred to herein as the "left section") of the inner surface of assembly 40.

In some embodiments, system 20 may comprise one or more mechanical-based and/or electrical-based control assemblies (not shown) that are respectively coupled, together or separately, to pulling wires 53, 54, 63 and 64.

In some embodiments, the control assemblies may be coupled to manipulator 32, e.g., as two separate control knobs, one for distal tip 50 and the other for flexible section 66. In these embodiments, physician 30 may use the control knobs to control the respective directions and levels of deflection of distal tip 50 and flexible section 66. In other embodiments, manipulator 32 may comprise any other suitable configuration of controlling features. Additionally or alternatively, the control assemblies may be controlled, using a suitable software, executed, for example, by processor 34 in control console 24.

In some embodiments, wire 53 is coupled to the inner surface of the right section of distal tip 50, at a coupling point 51. Similarly, wire 54 is coupled to the inner surface of the left section of distal tip 50, at a coupling point 52 facing coupling point 51.

In some embodiments, physician 30 may deflect distal tip 50 to a desired side by pulling a selected wire among wires 53 and 54. In the example of FIG. 2, physician 30 applied the respective control knob to pull wire 53, so as to apply bending force on distal tip 50, thereby to deflect assembly 40 to a desired spatial angle.

Reference is now made to an inset 58 showing a sectional top view AA of distal tip 50.

In the configuration of FIG. 2, distal tip 50 is deflectable in two dimensions indicated by the directions of arrows 59A and 59B. In some embodiments, physician 30 may deflect assembly 40 in other directions, relative to axis 55, by a combined operation that comprises both rotating distal end assembly 40 about axis 55, shown by an arrow 69, and pulling wire 53 or 54.

In other embodiments, assembly 40 may comprise any additional wires coupled to the inner surface of tip 50 at respective locations. For example, distal end assembly 40 may comprise two additional pulling wires (not shown) coupled to the inner surface of distal tip 50 at coupling points 56 and 57, thereby allowing deflection in directions indicated by respective arrows 67A and 67B.

In this configuration, physician 30 may pull, for example, two or more wires coupled to distal tip 50 at coupling points 52 and 51, so as to deflect the distal tip in a different direction indicated by an arrow 68, which is a sum of vectors of forces indicated by arrows 59A and 67B.

In alternative embodiments, any other suitable number of wires may be coupled to the inner surface of distal tip 50 at any suitable configuration. For example, the probe may comprise a single pulling wire and a rotation capability about axis 55. Note that the pulling wires may be coupled at the same sectional slice (e.g., section AA) or at different distance from the distal edge of assembly 40.

In some embodiments, distal end assembly 40 further comprises additional pulling wires, such as wires 63 and 64, coupled to flexible section 66 at respective coupling points 61 and 62. By pulling wire 63 or 64, physician can deflect flexible section 66 to the directions indicated by arrows 59B and 59A, respectively.

Note that flexible section 66 is typically less flexible than spring 60, so that the deflection level of flexible section 66 is lower compared to the deflection level of distal tip 50.

In other embodiments, any suitable number of pulling wires may be coupled at any other suitable location and angle to the inner surface of flexible section 66, instead of or in addition to wires 63 and 64.

In alternative embodiments, wires 53 and 54, and wires 63 and 64 may be coupled to the outer surfaces of distal tip 50 and flexible section 66, respectively, or at any other suitable locations.

In other embodiments, distal end assembly 40 may comprise one or more rigid wires in addition to, or instead of, some of the pulling wires. The rigid wires may be used for deflecting distal tip 50 relative to flexible section 66, and flexible section 66 relative to shaft 23, by applying, for example, a pushing force instead of, or in addition to, the pulling force described above.

The configuration of distal end assembly 40 shown in FIG. 2 is an example configuration, which is chosen purely for the sake of conceptual clarity. In alternative embodiments, any other suitable configuration can also be used.

For example, assembly 40 may comprise any suitable number of sections, such as distal tip 50 and flexible section 66, coupled along the longitudinal axis of catheter 22 at any suitable configuration. The sections may be coupled to one another using any suitable number and type of flexible elements, having any suitable degree of flexibility.

Although the embodiments described herein mainly address cardiac procedures, the methods and systems described herein can also be used in other applications, such as in sinuplasty, surgery, endoscopy, otolaryngology and neurology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical probe, comprising:

a shaft for navigation in a body, the shaft extending along a longitudinal axis and comprising a proximal end and a distal end;

a flexible section disposed on the distal end of the shaft;

a spring disposed on a distal end of the flexible section;

a rigid distal tip disposed on a distal end of the spring;

a first deflection mechanism comprising a first wire attached to a first side of the flexible section and a second wire attached to a second side of the flexible section, the first wire and the second wire each configured to deflect the flexible section relative to the shaft; and a second deflection mechanism comprising a third wire attached to a first side of the rigid distal tip and a fourth wire attached to a second side of the rigid distal tip, the third wire and the fourth wire each configured to deflect the rigid distal tip relative to the flexible section.

2. The medical probe of claim 1, wherein the first wire is configured to deflect the flexible section in a first direction relative to the longitudinal axis, and wherein the second wire is configured to deflect the flexible section in a second direction relative to the longitudinal axis, the second direction being opposite the first direction.

3. The medical probe of claim 2, wherein the third wire is configured to deflect the rigid distal tip in a third direction relative to the longitudinal axis, and wherein the fourth wire is configured to deflect the rigid distal tip in a fourth direction relative to the longitudinal axis, the fourth direction being opposite the third direction.

4. The medical probe of claim 3, wherein the first direction, the second direction, the third direction, and the fourth direction are each different from one another.

5. The medical probe of claim 1 further comprising a medical device attached to the rigid distal tip, the medical device comprising a plurality of electrodes configured to detect electrical-potential signals of a heart.

6. The medical probe of claim 1 further comprising a medical device attached to the rigid distal tip, the medical device comprising a plurality of electrodes configured for ablation of tissue of a heart.

7. The medical probe of claim 1, wherein the flexible section is less flexible than the spring.

8. The medical probe of claim 1 further comprising a handle, wherein the first wire, the second wire, the third wire, and the fourth wire are each attached to the handle.

9. The medical probe of claim 8, wherein the handle comprises a first device configured to apply a first force to the first wire and a second force to the second wire to cause deflection of the flexible section, and wherein the handle comprises a second device configured to apply a third force to the third wire and a fourth force to the fourth wire to cause deflection of the rigid distal tip.

10. The medical probe of claim 1, wherein the shaft, the flexible section, the spring, and the rigid distal tip form a hollow profile and the first wire, the second wire, the third wire, and the fourth wire are each disposed within the hollow profile.

* * * * *